United States Patent
Nishiwaki

[11] Patent Number: 6,128,088
[45] Date of Patent: Oct. 3, 2000

[54] VISIBILITY RANGE MEASURING APPARATUS FOR MOTOR VEHICLE

[75] Inventor: Takeshi Nishiwaki, Tokyo, Japan

[73] Assignee: Mitsubishi Denki Kabushiki Kaisha, Tokyo, Japan

[21] Appl. No.: 09/187,409

[22] Filed: Nov. 6, 1998

[30] Foreign Application Priority Data

May 12, 1998 [JP] Japan ................................. 10-128628

[51] Int. Cl.[7] .............................. G01B 9/08; G01C 3/00
[52] U.S. Cl. ................................................ 356/392; 356/3
[58] Field of Search ..................... 356/392, 375, 356/384, 385, 3; 340/901, 937, 942; 348/135, 143, 148

[56] References Cited

U.S. PATENT DOCUMENTS

| | | | |
|---|---|---|---|
| 5,307,136 | 4/1994 | Saneyoshi | 356/1 |
| 5,351,044 | 9/1994 | Mathur et al. | 340/901 |
| 5,739,848 | 4/1998 | Shimoura et al. | 348/119 |

FOREIGN PATENT DOCUMENTS 6-75036   9/1994   Japan.

*Primary Examiner*—Frank G. Font
*Assistant Examiner*—Michael P. Stafira
*Attorney, Agent, or Firm*—Sughrue, Mion, Zinn, Macpeak & Seas, PLLC

[57] ABSTRACT

A visibility range measuring apparatus for detecting visibility range in a passive fashion without suffering erroneous operation even in the case of such a situation that a plurality of visibility range measuring apparatuses exist within a coverage thereof. The apparatus includes a camera mounted on a motor vehicle for taking a picture of parts of a lane-dividing mark lines extending forwardly in front of a motor vehicle and a visibility-range determining control unit for determining the visibility range through comparison of luminances at a plurality of locations of the lane-dividing mark line, which locations differ from one another with respect to the location of the motor vehicle.

4 Claims, 5 Drawing Sheets

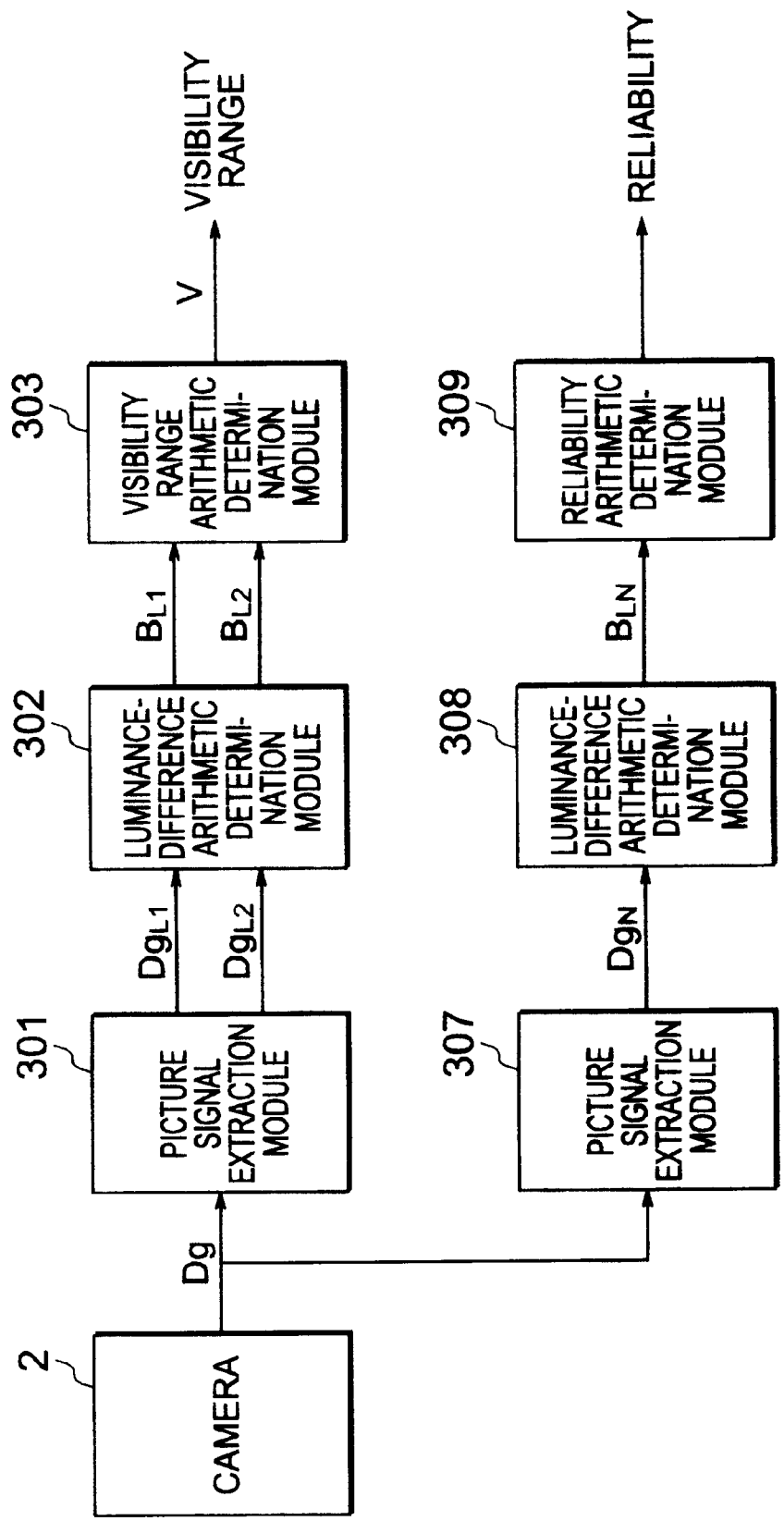

VISIBILITY RANGE MEASURING APPARATUS FOR MOTOR VEHICLE

BACKGROUND OF THE INVENTION

1. Field of the Invention

The present invention relates to a visibility range measuring apparatus, i.e., apparatus for measuring the range of visibility, for a motor vehicle or the like.

2. Description of Related Art

The visibility range measuring apparatus such as mentioned above is already known, as is disclosed in Japanese Patent Publication No. 75036/1994 (JP-6-75036). The conventional visibility range measuring apparatus includes a light projector or emitter for projecting or emitting light pulses or flashing light and a processing unit for determining or measuring the visibility range by making use of the light undergone back scattering at regions or sections located on an optical path along which the light pulses or flashing light are emitted or projected.

The conventional visibility range measuring apparatus for a motor vehicle however suffers a problem that the visibility range may possibly be measured erroneously due to interference of the light pulses or flashing light emitting from another visibility range measuring apparatus mounted on a motor vehicle traveling, for example, in the opposite direction, because the visibility range measuring apparatus known heretofore is so arranged as to emit light pulses or flashing light for thereby measuring the visibility range on the basis of the reflection or echo light.

SUMMARY OF THE INVENTION

In the light of the state of the art described above, it is an object of the present invention to provide a visibility range measuring apparatus for a motor vehicle which is capable of measuring the visibility range with high accuracy and enhanced reliability even in the case where a plurality of visibility range measuring apparatuses exist concurrently within a coverage of these apparatuses, to thereby solve the problem of the conventional visibility range measuring apparatus mentioned above.

In view of the above and other objects which will become apparent as the description proceeds, there is provided according to a general aspect of the present invention a visibility range measuring apparatus for a motor vehicle, which apparatus includes a picture pickup means or camera mounted on the motor vehicle for taking a picture of a lane-dividing mark line on a road, a luminance detecting means for detecting luminances of the lane-dividing mark line relative to a background luminance at different locations of the lane-dividing mark line distanced from the motor vehicle by different distances, respectively, on the basis of a picture signal outputted from the picture pickup means, and a visibility range determining means for determining the visibility range through comparison of the luminances detected by the luminance detecting means.

By virtue of the arrangement described above, the visibility range can be determined on the basis of the picture signal of the lane-dividing mark line on the road as picked up by the picture pickup means or camera. Accordingly, even in the case where other visibility range measuring apparatus or apparatuses of a similar type exist within a coverage of the visibility range measuring apparatus of concern, the visibility range can be measured with high reliability without being subjected to adverse influence of mutual interference.

In a preferred mode for carrying out the invention, the visibility range determining means may be so arranged as to perform comparison of luminances of the lane-dividing mark line detected by the visibility range determining means on a plurality of combinations of the luminances, to thereby determine the visibility range on the basis of a mean value of visibility range candidate values as determined through the comparison.

With the arrangement described above, the influence of variation in the detected luminance due to partial or local contamination of the lane-dividing mark line can be suppressed, whereby measurement of the visibility range can be accomplished with high accuracy and reliability essentially independent of the states of the lane-dividing mark line.

In another preferred mode for carrying out the invention, the visibility range determining means may be so arranged as to perform comparison of luminances of the lane-dividing mark line detected by the visibility range determining means on three or more combinations of luminances to thereby determine the visibility range on the basis of a mean value of visibility range candidate values as determined through the comparison, wherein the visibility range is determined on the basis of a mean value of visibility range candidate values exclusive of those whose luminances differ significantly from the mean value of the visibility range candidate values.

By virtue of the arrangement described above, the influence of variation in the detected luminance due to partial or local contamination of the lane-dividing mark line can be suppressed, whereby measurement of the visibility range can be accomplished with high accuracy and reliability substantially independent of the states of the lane-dividing mark line.

In a further preferred mode for carrying out the invention, the visibility range measuring apparatus mentioned above may further include a reliability decision means for determining reliability of the visibility range measured by the visibility range measuring apparatus on the basis of luminances of the lane-dividing mark line as detected.

With the arrangement mentioned above, there can be detected such abnormal or unfavorable state that sufficiently high luminance of the lane-dividing mark line can not be detected from the picture signal due to insufficient illumination, whereby the information of power reliability of the measured visibility range can be made available.

The above and other objects, features and attendant advantages of the present invention will more easily be understood by reading the following description of the preferred embodiments thereof taken, only by way of example, in conjunction with the accompanying drawings.

BRIEF DESCRIPTION OF THE DRAWINGS

In the course of the description which follows, reference is made to the drawings, in which:

FIG. 5 is a functional block diagram for illustrating generally and schematically a processing procedure executed by a visibility range determining control unit in the visibility range measuring apparatus according to a fourth embodiment of the present invention.

DESCRIPTION OF THE PREFERRED EMBODIMENTS

Figure 1:
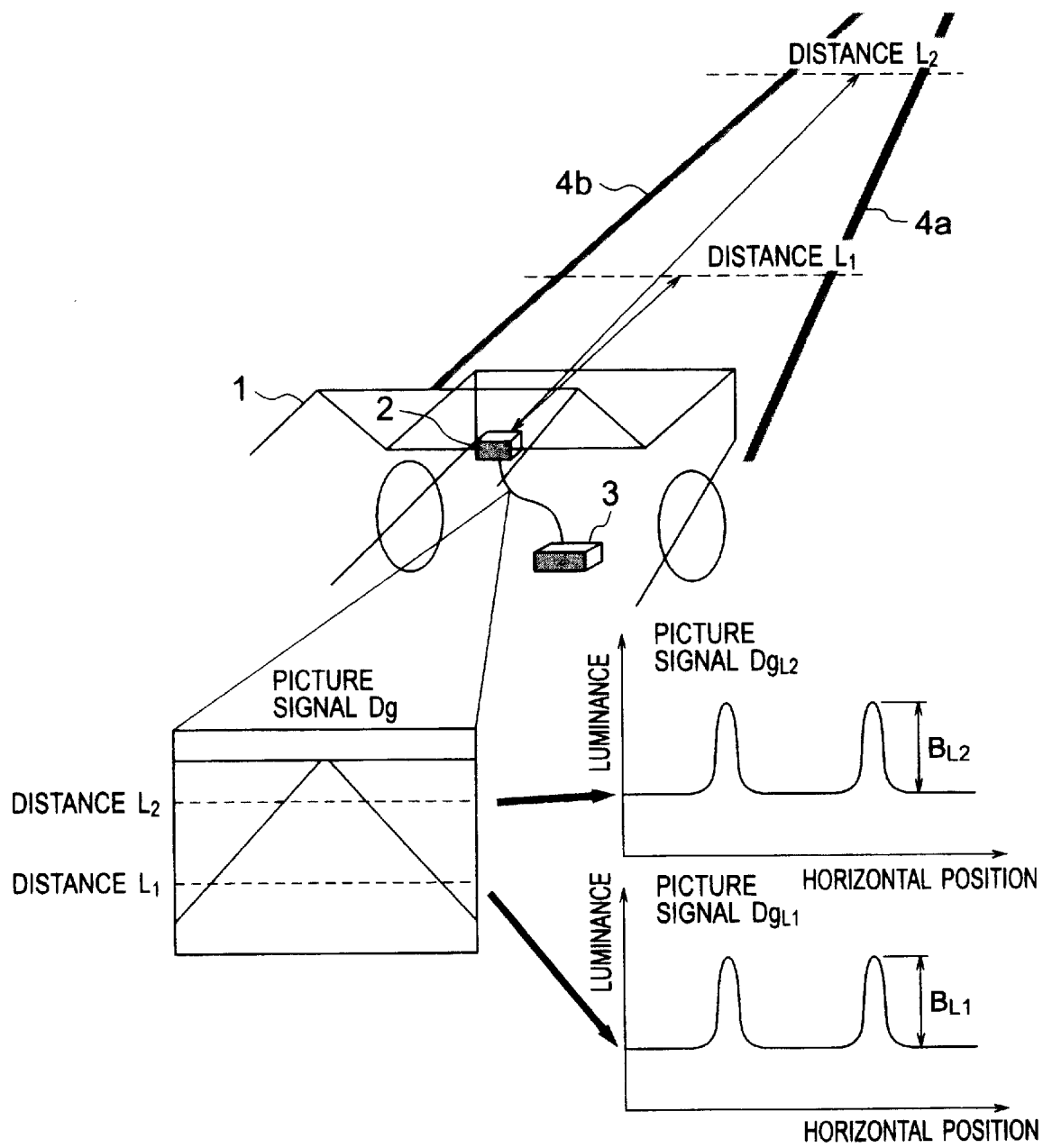
FIG. 1 is a diagram showing generally and schematically a system configuration of a visibility range measuring apparatus according to an embodiment of the invention.

The present invention will now be described in detail in conjunction with what is presently considered as preferred or typical embodiments thereof by reference to the drawings. In the following description, like reference characters designate like or corresponding parts throughout the several views. Further, it should be understood that the term "motor vehicle" is used to encompass not only the automobile in the intrinsic sense but also other vehicles such as truck, bus or similar motor- or engine-driven conveyances.

Embodiment 1

Now, the visibility range measuring apparatus according to a first embodiment of the present invention will be described. FIG. 1 is a diagram showing generally and schematically a system configuration of a visibility range measuring apparatus for a motor vehicle according to an embodiment of the invention. Referring to the figure, a picture pickup means or camera for taking a picture of a lane-dividing mark line or lines painted on a road is mounted on a motor vehicle for measuring luminances $B_{L1}$ and $B_{L2}$ of lane-dividing mark line picture signal corresponding to a plurality of points or locations on the lane-dividing mark line, respectively. The range of visibility, i.e., visibility range is arithmetically determined on the basis of luminances detected from the picture signal. More specifically, in FIG. 1, reference numeral 1 denotes a motor vehicle which is equipped with the visibility range measuring apparatus according to the present invention, reference characters 4a and 4b denote lane-dividing mark lines, respectively, which are painted on a road, reference numeral 2 denotes a picture pickup means or camera which is disposed so that a horizontal image pickup direction thereof extends substantially in parallel with a surface of the road for taking a picture of the lane-dividing mark lines 4a and 4b on the road, reference character Dg designates a picture signal outputted from the camera 2. Further, reference numeral 3 denotes generally a visibility range determining control unit for arithmetically determining a visibility range by extracting component picture signals $Dg_{L1}$ and $Dg_{L2}$ corresponding to the ranges or distances from the picture signal Dg outputted from the camera 2, and reference characters $B_{L1}$ and $B_{L2}$ designate luminances of the lane-dividing mark lines, respectively, relative to the background luminance at given distances $L_1$ and $L_2$ in the forward direction of the motor vehicle. To say in another way, the reference characters $B_{L1}$ and $B_{L2}$ represent, respectively, differences in luminance between the lane-dividing mark lines and the background luminance.

Figure 2:
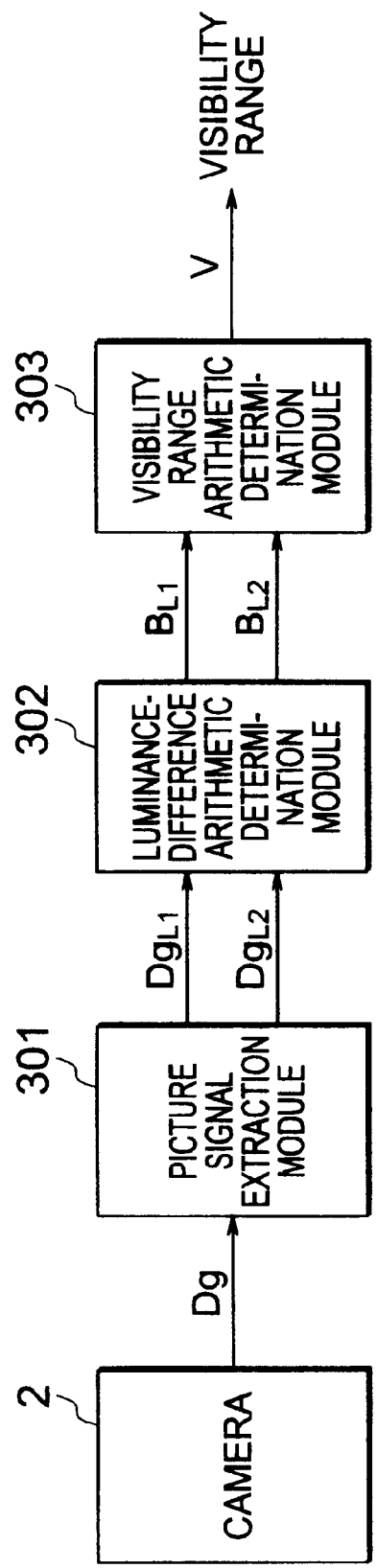
FIG. 2 is a functional block diagram for illustrating schematically a processing procedure performed by a visibility range determining control unit incorporated in the visibility range measuring apparatus according to a first embodiment of the present invention.

The picture signal outputted from the picture pickup means or camera 2 is inputted to the visibility range determining control unit 3. FIG. 2 is a functional block diagram for illustrating schematically a processing procedure performed by the visibility range determining control unit 3. Referring to FIG. 2, a picture signal extraction module 301 designated for extracting a picture signal at a portion remote therefrom by a distance for visibility range determination is designed to extract from the picture signal Dg the fragmental picture signals $Dg_{L1}$ and $Dg_{L2}$ of corresponding portions or locations of the lane-dividing mark line(s) distanced from the camera by distances $L_1$ and $L_2$, respectively. The fragmental picture signals $Dg_{L1}$ and $Dg_{L2}$ thus extracted are then inputted to a luminance-difference arithmetic determination module 302. In the luminance-difference arithmetic determination module 302, luminance differences $B_L$ between the background luminance and the luminances of the lane-dividing mark lines 4a and 4b, respectively, are arithmetically determined, the results of which are inputted to a visibility range arithmetic determination module 303. The visibility range arithmetic determination module 303 is so designed as to arithmetically determine the visibility range V on the basis of luminance differences $B_{L1}$ and $B_{L2}$ inputted from the luminance-difference arithmetic determination module 302 in accordance with the following expression (1).

$$V=\{(L_1-L_2)\cdot ln(1/\epsilon_0)\}/ln(B_{L1}/B_{L2}) \tag{1}$$

Next, a method of deriving the above expression (1) will be described.

In general, it is known that attenuation coefficient σ of the light ray in the favorable ambient condition with the transmittance being approximately equal to 1 (one) can be determined on the basis of luminance $B_{L1}$ of the lane-dividing mark line in the picture signal corresponding to a point or location in front of the camera remote therefrom by a certain distance $L_1$ and luminance $B_{L2}$ of the lane-dividing mark line in the picture signal corresponding to a point or location in front of the camera remote therefrom by a certain distance $L_2$ in accordance with the following expressions (2) and (3):

$$\sigma_1=L_1^{-1}ln(B_{c1}/B_{L1}) \tag{2}$$

$$\sigma_2=L_2^{-1}ln(B_{c2}/B_{L2}) \tag{3}$$

In general, luminance $B_c$ of the lane-dividing mark line in the favorable environmental condition with the transmittance being approximately equal to 1 (one) is constant when the lane-dividing mark line exhibits uniformity. Accordingly, the luminance $B_{c1}$ may be regarded to be equal to the luminance $B_{c2}$. Thus, by representing $B_{c1}$ and $B_{c2}$ generally by $B_c$, i.e., $B_c=B_{c1}=B_{c2}$, then the above expressions (2) and (3) may be rewritten in a general form as follows: $\sigma=\sigma_1-\sigma_2$, thus $$\sigma=(L_1-L_2)^{-1}ln(B_{L1}/B_{L2}) \tag{4}$$

Similarly, it is also generally known that the visibility range V can be determined on the basis of the attenuation coefficient σ of the light ray in accordance with the following expression (5):

$$V=ln(1/\epsilon_0)/\sigma \tag{5}$$

From the above expressions (4) and (5), the visibility range V can be determined in accordance with the under-mentioned expression (6) on the basis of the luminance $B_{L1}$ of the lane-dividing mark line in the picture signal at a location corresponding to a point in front of the camera remote therefrom by a certain distance $L_1$ and the luminance $B_{L2}$ of the lane-dividing mark line in the picture signal at a location corresponding to a point in front of the camera remote therefrom by a certain distance $L_2$. Namely, $$V = \{(L_1 - L_2) \cdot ln(1/\epsilon_0)\} / ln(B_{L1}/B_{L2}) \quad (6)$$

Needless to say, the above expression (6) is identical with the previously mentioned expression (1). In other words, the visibility range V can be determined in accordance with the expression (1).

Embodiment 2

Figure 3:
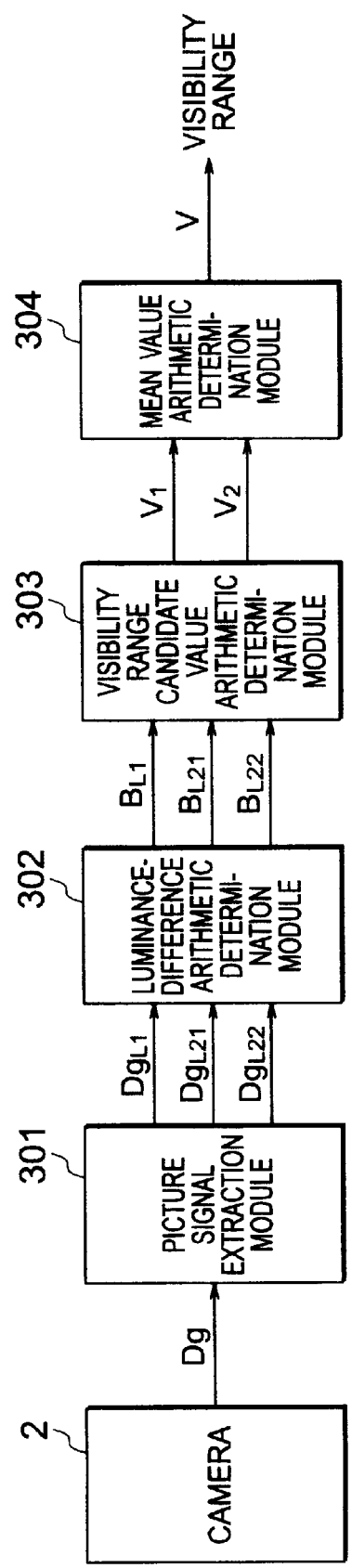
FIG. 3 is a functional block diagram for illustrating generally and schematically a processing procedure executed by a visibility range determining control unit incorporated in the visibility range measuring apparatus according to a second embodiment of the present invention.

A second embodiment of the present invention will be described. The visibility range measuring apparatus according to the second embodiment is implemented essentially in a same structure as the visibility range measuring apparatus shown in FIG. 1. FIG. 3 is a functional block diagram for illustrating generally a processing procedure executed by the visibility range measuring apparatus according to the instant embodiment of the invention. In general, the visibility range measuring apparatus according to the instant embodiment is so designed as to arithmetically determine the visibility range on the basis of a mean value of plural visibility ranges V as determined. Referring to FIG. 3, the picture signal extraction module 301 extracts from the picture signal Dg fragmental picture signals $Dg_{L1}$, $Dg_{L21}$ and $Dg_{L22}$ of those portions of the lane-dividing mark lines which are remote from the camera by distances $L_1$, $L_{21}$ and $L_{22}$, respectively. The picture signal components $Dg_{L1}$, $Dg_{L21}$ and $Dg_{L22}$ extracted are inputted to a luminance-difference arithmetic determination module 302.

In the luminance-difference arithmetic determination module 302, luminance differences $B_L$ between the background luminance and the luminances of the lane-dividing mark lines, respectively, are arithmetically determined, whereon the luminance differences $B_{L1}$, $B_{L21}$ and $B_{L22}$ as determined are inputted to a visibility range candidate value arithmetic determination module 303. In the visibility range candidate value arithmetic determination module 303, the visibility range candidate values $V_1$ and $V_2$ are determined on the basis of differences between the luminance difference signals $B_{L1}$ and $B_{L21}$ and between the luminance difference signals $B_{L1}$ and $B_{L22}$, respectively, in accordance with the expression (1) or the expression (6) mentioned previously. The visibility range candidate values $V_1$ and $V_2$ are then inputted to a mean value arithmetic determination module 304, which determines the visibility range by averaging the visibility range candidate values $V_1$ and $V_2$.

Embodiment 3

Figure 4:
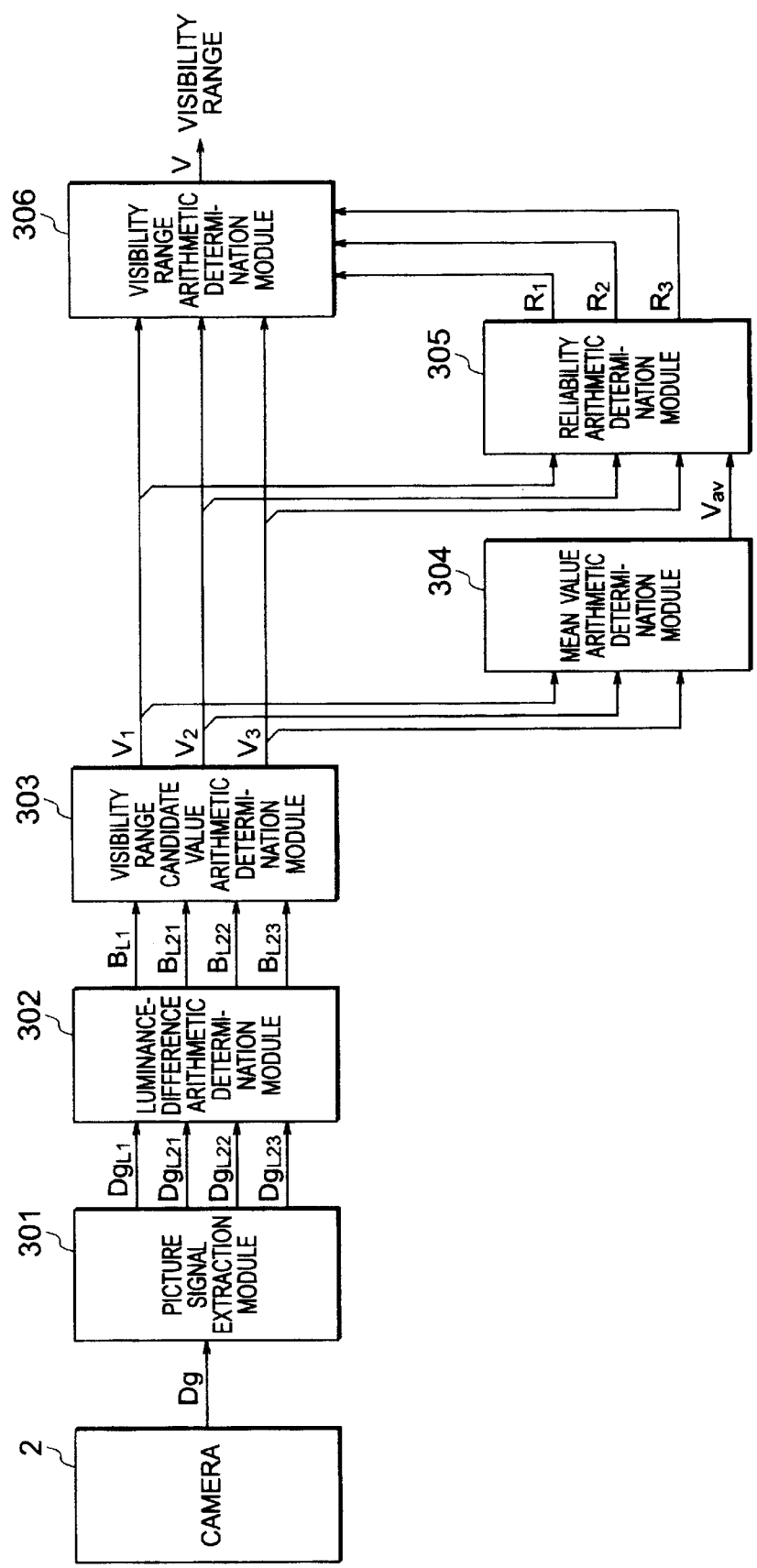
FIG. 4 is a functional block diagram for illustrating generally and schematically a processing procedure executed by a visibility range determining control unit incorporated in the visibility range measuring apparatus according to a third embodiment of the present invention.

A third embodiment of the present invention will be described. The visibility range measuring apparatus according to the third embodiment is implemented substantially in a similar configuration as the visibility range measuring apparatus according to the first embodiment shown in FIG. 1. FIG. 4 is a functional block diagram for illustrating generally a processing procedure executed by the visibility range measuring apparatus according to the instant embodiment of the invention. In general, the visibility range measuring apparatus according to the instant embodiment of the invention is so designed as to perform arithmetic determination for determining the visibility range V on the basis of a plurality of combinations of the luminance signals except for those differing remarkably from a mean value $V_{av}$ of the visibility range candidate values $V_1$, $V_2$ and $V_3$ to thereby determine the visibility range V on the basis of the mean value of the selected or valid luminance signals. Referring to FIG. 4, the picture signal extraction module 301 extracts from the picture signal Dg the fragmental picture signals $Dg_{L1}$, $Dg_{L21}$, $Dg_{L22}$ and $Dg_{L23}$ of those portions of the lane-dividing mark lines which are remote from the camera by distances $L_1$, $L_{21}$, $L_{22}$ and $L_{23}$, respectively. The fragmental picture signals $Dg_{L1}$, $Dg_{L21}$, $Dg_{L22}$ and $Dg_{L23}$ as extracted are inputted to a luminance-difference arithmetic determination module 302.

More specifically, in the luminance-difference arithmetic determination module 302, luminance differences $B_L$ between the background luminance and the luminances of the lane-dividing mark lines at the corresponding points or locations thereof, respectively, are arithmetically determined, whereon the luminance difference signals $B_{L1}$, $B_{L21}$, $B_{L22}$ and $B_{L23}$ as determined are inputted to the visibility range candidate value arithmetic determination module 303. In the visibility range candidate value arithmetic determination module 303, the visibility range candidate values $V_1$, $V_2$ and $V_3$ are determined on the basis of the combinations of the luminance difference $B_{L1}$ and luminance differences $B_{L21}$, $B_{L22}$ and $B_{L23}$, respectively, (which are inputted from the luminance-difference arithmetic determination module 302) in accordance with the expression (1) or (6) mentioned previously. The visibility range candidate values $V_1$, $V_2$ and $V_3$ are then inputted to a mean value arithmetic determination module 304 and hence to, a reliability arithmetic determination module 305 and a visibility range arithmetic determination module 306.

In the mean value arithmetic determination module 304, a mean value $V_{av}$ of the visibility range candidate values $V_1$, $V_2$ and $V_3$ is determined to be supplied to the reliability arithmetic determination module 305. In the reliability arithmetic determination module 305, the visibility range candidate values $V_1$, $V_2$ and $V_3$ inputted from the visibility range candidate value arithmetic determination module 303 are each divided by the mean value $V_{av}$ inputted from the mean value arithmetic determination module 304. When the values resulting from the division mentioned above fall within predetermined ranges, respectively, the reliability arithmetic determination module 305 decides that the visibility range candidate value is valid. If otherwise, the visibility range candidate value is decided to be invalid. In dependence on the results of the decision, the reliability arithmetic determination module 305 outputs signals $R_1$, $R_2$ and $R_3$ indicating validity or invalidity of the visibility range candidate values $V_1$, $V_2$ and $V_3$, respectively. The signals $R_1$, $R_2$ and $R_3$ are supplied to the visibility range arithmetic determination module 306.

In the visibility range arithmetic determination module 306, the visibility range V is arithmetically determined by averaging those of the visibility range candidate values $V_1$, $V_2$ and $V_3$ which are supplied from the visibility range candidate module arithmetic determination module 303 and decided to be valid in dependence on the signals $R_1$, $R_2$ and $R_3$, respectively, supplied from the reliability arithmetic determination module 305.

Embodiment 4

A fourth embodiment of the present invention will be described. The visibility range measuring apparatus according to the fourth embodiment is implemented essentially in a similar structure as that shown in FIG. 1. FIG. 5 is a functional block diagram for illustrating generally a processing procedure for checking the reliability of the determined visibility range value on the basis of the luminances at locations of the lane-dividing mark line which are located near to the motor vehicle and which are at levels higher than a given one. Referring to FIG. 5, a picture signal extraction module 301 is designed to extract from a picture signal Dg the fragmental picture signals $Dg_{L1}$ and $Dg_{L2}$ of corresponding portions or locations of the lane-dividing mark line distanced from the camera 2 by distances $L_1$ and $L_2$, respectively. The fragmental picture signals $Dg_{L1}$ and $Dg_{L2}$ thus extracted are then inputted to the luminance-difference arithmetic determination module 302.

In the luminance-difference arithmetic determination module 302, luminance differences $B_L$ between the background luminance and the luminances of the lane-dividing mark lines, respectively, are arithmetically determined, the results of which are inputted to the visibility range arithmetic determination module 303. The visibility range arithmetic determination module 303 is so designed as to arithmetically determine the visibility range V on the basis of luminance difference signals $B_{L1}$ and $B_{L2}$ supplied from the luminance-difference arithmetic determination module 302 in accordance with the expression (1) and hence expression (6) mentioned previously.

On the other hand, in the picture signal extraction module 307, the picture signal $D_{JN}$ of a lane-dividing mark line portion located in the vicinity of the camera 2 is extracted from the picture signal Dg to be supplied to a luminance-difference arithmetic determination module 308. In the luminance-difference arithmetic determination module 308, the luminance difference $B_{LN}$ between the background luminance and the luminance of the lane-dividing mark line is determined to be inputted to a reliability arithmetic determination module 309, which then compares the luminance difference $B_{LN}$ with a predetermined value to thereby make a decision as to the reliability of the output value indicating the visibility range currently being measured.

Many features and advantages of the present invention are apparent from the detailed description and thus it is intended by the appended claims to cover all such features and advantages of the apparatuses which fall within the true spirit and scope of the invention. Further, since numerous modifications and combinations will readily occur to those skilled in the art, it is not intended to limit the invention to the exact construction and operation illustrated and described.

By way of example, although the description has been made on the assumption that the visibility range measuring apparatus is comprised of discrete modules, it should be understood that the control unit of the visibility range measuring apparatus can be implemented as a microcomputer or processor implemented in an IC structure and that the processings described in the foregoing may be executed by resorting to software or program to be executed by the control unit.

Accordingly, all suitable modifications and equivalents may be resorted to, falling within the spirit and scope of the invention.

What is claimed is:

1. A visibility range measuring apparatus for a motor vehicle, comprising:

picture pickup means mounted on said motor vehicle for taking a picture of a lane-dividing mark line on a road;

luminance detecting means for detecting luminances of said lane-dividing mark line relative to a background luminance at different locations of said lane-dividing mark line located away from said motor vehicle at different distances, respectively, on the basis of a picture signal outputted from said picture pickup means; and visibility range determining means for determining the visibility range by comparing said luminances detected by said luminance detecting means.

2. A visibility range measuring apparatus for a motor vehicle according to claim 1, wherein said visibility range determining means performs the comparison on a plurality of combinations of said luminances to thereby determine visibility range candidate values, and wherein said visibility range is determined on the basis of a mean value of said visibility range candidate values.

3. A visibility range measuring apparatus for a motor vehicle according to claim 1, wherein said visibility range determining means performs the comparison on three or more combinations of said luminances to thereby determine visibility range candidate values, and wherein said visibility range is determined on the basis of a mean value of said visibility range candidate values exclusive of those whose luminances differ significantly from said visibility range candidate values.

4. A visibility range measuring apparatus for a motor vehicle according to claim 1, further comprising:

reliability decision means for determining the reliability of said visibility range measured by said visibility range measuring apparatus on the basis of said detected luminances of said lane-dividing mark line.

* * * * *